United States Patent [19]
Sankey et al.

[11] 3,941,796
[45] Mar. 2, 1976

[54] α-(HYDROXY AND ALKOXY SUBSTITUTED)PHENYL-α-(2-PIPERIDINYL)-METHANOLS

[75] Inventors: George H. Sankey, Loughborough; Keith D. E. Whiting, Hatfield, both of England

[73] Assignee: Minnesota Mining and Manufacturing Company, St. Paul, Minn.

[22] Filed: July 11, 1974

[21] Appl. No.: 487,661

Related U.S. Application Data

[63] Continuation-in-part of Ser. No. 39,571, May 21, 1970, abandoned.

[52] U.S. Cl................................. 260/293.84; 424/267
[51] Int. Cl.²........................................ C07D 211/22
[58] Field of Search................... 260/293.83, 293.84

[56] References Cited
UNITED STATES PATENTS 3,705,169   12/1972   Kaiser et al.................... 260/293.84

*Primary Examiner*—G. Thomas Todd
*Attorney, Agent, or Firm*—Alexander, Sell, Steldt & DeLaHunt

[57] ABSTRACT

α-(Hydroxy and alkoxy substituted)phenyl-α-(2-piperidinyl)methanols of the formula

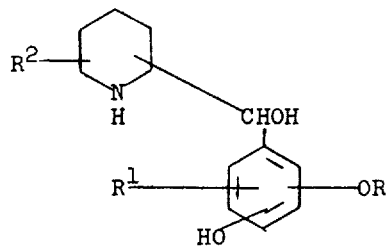

where R is hydrogen or lower alkyl, $R^1$ is hydrogen, hydroxy or lower alkoxy, and $R^2$ is phenyl, phenyl-lower alkyl, diphenyl-lower alkyl, phenoxy-lower alkyl or diphenoxy-lower alkyl, and the non-toxic pharmaceutically acceptable acid-addition and quaternary ammonium salts thereof.

7 Claims, No Drawings

α-(HYDROXY AND ALKOXY SUBSTITUTED)PHENYL-α-(2-PIPERIDINYL)-METHANOLS

RELATED APPLICATIONS

This application is a continuation-in-part of a copending application U.S. Ser. No. 39,571 filed May 21, 1970, now abandoned.

BACKGROUND OF THE INVENTION

The compounds of the invention are in the field of phenyl-(2-piperidinyl)methanols.

Compounds of the general type are known, e.g., phenylpiperidinylmethanol derivatives in which the phenyl group is substituted in the 4-position by a halogen, lower alkyl, lower alkoxy or methylenedioxy group as described in U.S. Pat. No. 2,928,835. The compound wherein the phenyl ring is 3,4-dimethoxy-substituted is described in British Pat. No. 843,070. The corresponding m-or p-hydroxyphenyl-2-piperidinylmethanols are described in Diss. Abstr. B, 28, No. 7, 2781–2784, Univ. Mich, 1966, the unsubstituted compound α-phenyl-α-(2-piperidinyl)methanol is disclosed in British Pat. No. 994,964.

While the compounds described in the above references have physiological activity, they are not known to possess utility as bronchodilator agents.

U.S. Pat. No. 3,705,169 discloses compounds active as bronchodilators wherein an unsubstituted piperidinyl ring is bonded through a hydroxymethyl group to a substituted phenyl ring. However, compounds of the present invention are structurally distinct from the compounds disclosed by this reference in that the present compounds contain an aryl substituted piperidinyl ring. In addition, compounds of the present invention exhibit a significantly longer duration of activity as compared to compounds of this reference, when administered orally to protect against histamine-induced bronchial spasm in animals.

DETAILED DESCRIPTION OF THE INVENTION

This invention relates to substituted α-phenyl-α-(2-piperidinyl)methanols, to processes for the preparation thereof and to the use of these compounds and pharmaceutical compositions containing them as bronchodilator agents.

The chemical compounds of the invention have the formula

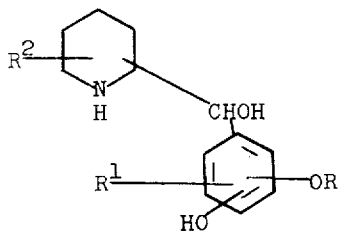

wherein R is hydrogen or lower alkyl; $R^1$ is hydrogen, hydroxy or lower alkoxy; and $R^2$ is phenyl, phenyl-lower alkyl, diphenyl-lower alkyl, phenoxy-lower alkyl or diphenoxy-lower alkyl. Preferred compounds of the invention are those wherein the phenyl ring is substituted by at least two hydroxy groups in either the 3 or 5 positions or the 3 and 4 positions.

Compounds wherein $R^2$ is in the 6 position of the piperidine ring are preferred. Preferred substituents are phenyl-lower alkyl and diphenyl-lower alkyl.

Preferred compounds of the invention include:
α-(3,4-dihydroxyphenyl)-α-(6-phenethyl-2-piperidinyl)methanol,
α-(3,4-dihydroxyphenyl)-α-(6-dibenzylmethyl-2-piperidinyl)methanol,
α-(3,5-dihydroxyphenyl)-α-(6-phenethyl-2-piperidinyl)methanol,
α-(3,5-dihydroxyphenyl)-α-(6-benzyl-2-piperidinyl)-methanol and pharmaceutically acceptable salts thereof.

As used herein, the terms "lower alkyl" and "lower alkoxy" embrace both straight and branched chain alkyl radicals containing from 1 to 6 carbon atoms and cycloalkyl radicals containing from 3 to 6 carbon atoms.

Compounds of the invention can be converted to their pharmaceutically acceptable acid-addition and quaternary ammonium salts if desired. These salts are included within the scope of the invention since they possess utility comparable to the free base compounds and may be used in place thereof.

"Pharmaceutically acceptable" salts are those which are not substantially more toxic than the compounds themselves, and which are capable of incorporation into conventional solid and liquid pharmaceutical carriers. Acid addition salts such as the hydrochloride, hydrobromide, hydroiodide, sulfate, phosphate, nitrate or the like may be formed with inorganic acids. Salts may also be formed with organic acids including monobasic acids to form salts such as the acetate, benzoate or the propionate. Especially preferred salts are those formed with hydroxy organic acids and dibasic acids such as ascorbic, oxalic, lactic, fumaric, citric, tartaric, malic and maleic acids. Useful quaternary ammonium salts include those formed by such alkyl halides as methyl iodide, n-hexylbromide and the like. Compounds of the invention may be present as diastereoisomers. These are designated as erythro- and threo-isomers which may be resolved as d,l optical isomers. Unless otherwise specified herein, all isomers of compounds whether separated or mixtures thereof, are comprehended within the scope of the specification and claims.

The compounds of the invention are prepared by several processes. Each requiring a sequence of reaction steps.

Process I is illustrated by the following reaction sequence:

Process I:

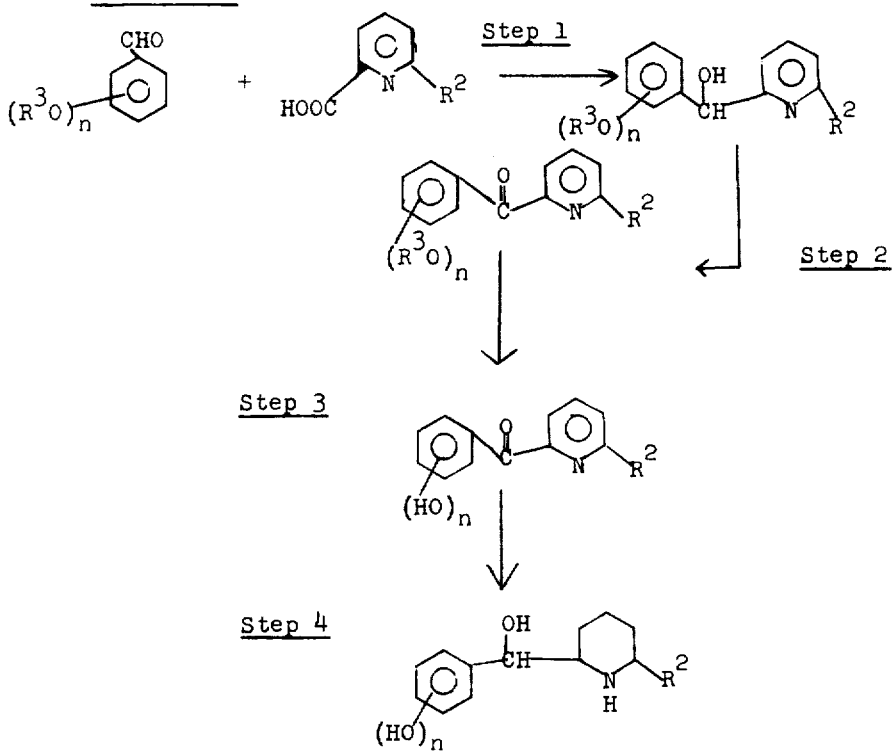

wherein $R^3$ is lower alkyl, $n$ is 2 or 3 and $R^2$ is phenyl, phenyl-lower alkyl, diphenyl-lower alkyl, phenoxy-lower alkyl or diphenoxy-lower alkyl.

Step 1 comprises condensing a poly-lower alkoxy substituted benzaldehyde with a 6-substituted pyridine-carboxylic acid to form an α-(poly-lower alkoxyphenyl)-α-(6-substituted-2-pyridinyl)methanol intermediate. In Step 2 this methanol intermediate is oxidized to form an α-(poly-lower alkoxyphenyl) (6-substituted-2-pyridyl) ketone intermediate. The ketone intermediate is dealkylated in Step 3 to form the corresponding (polyhydroxy-phenyl) (6-substituted-2-pyridyl) ketone intermediate. In Step 4 this intermediate is hydrogenated to give the α-(polyhydroxyphenyl)-α-(6-substituted-2-piperidinyl)methanol final product.

Process II for preparing compounds of the invention is illustrated by the following reaction sequence.

wherein $R^3$ is lower alkyl, $m$ is 1 or 2 and $R^2$ is phenyl, phenyl-lower alkyl, diphenyl-lower alkyl, phenoxy-lower alkyl or diphenoxy-lower alkyl.

Step 1 comprises treating a lower alkoxy-substituted p-benzyloxybenzaldehyde (or di- or tri-alkoxy-substituted benzaldehyde) with a 6-substituted-2-pyridyllithium reagent to form an α-(lower-alkoxy-p-benzyloxyphenyl)-α-(6-substituted-2-pyridinyl)methanol intermediate. In Step 2 the benzyl protecting group is removed from this intermediate by hydrogenation in the presence of e.g., palladium catalyst to form an α-(lower-alkoxy-p-hydroxyphenyl)-α-(6-substituted-2-pyridinyl)methanol intermediate. This methanol intermediate is hydrogenated in Step 3 to form the α-(lower-alkoxy-p-hydroxyphenyl)-α-(6-substituted-2-piperidinyl)-methanol final product.

Process II:

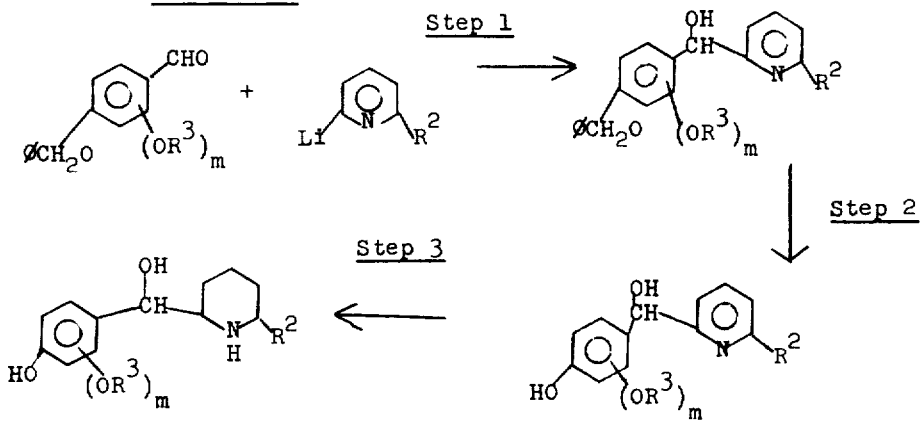

Process III for preparing the compounds of the invention wherein $R^2$ is phenyl-lower alkyl or diphenyl-lower alkyl is is illustrated by the following reaction sequence:

wherein $R^2$ is phenoxy-lower alkyl or diphenoxy-lower alkyl, it may be preferred to use as starting materials poly(benzyloxy)-substituted benzaldehydes rather than polyalkoxy substituted benzaldehydes in Processes I

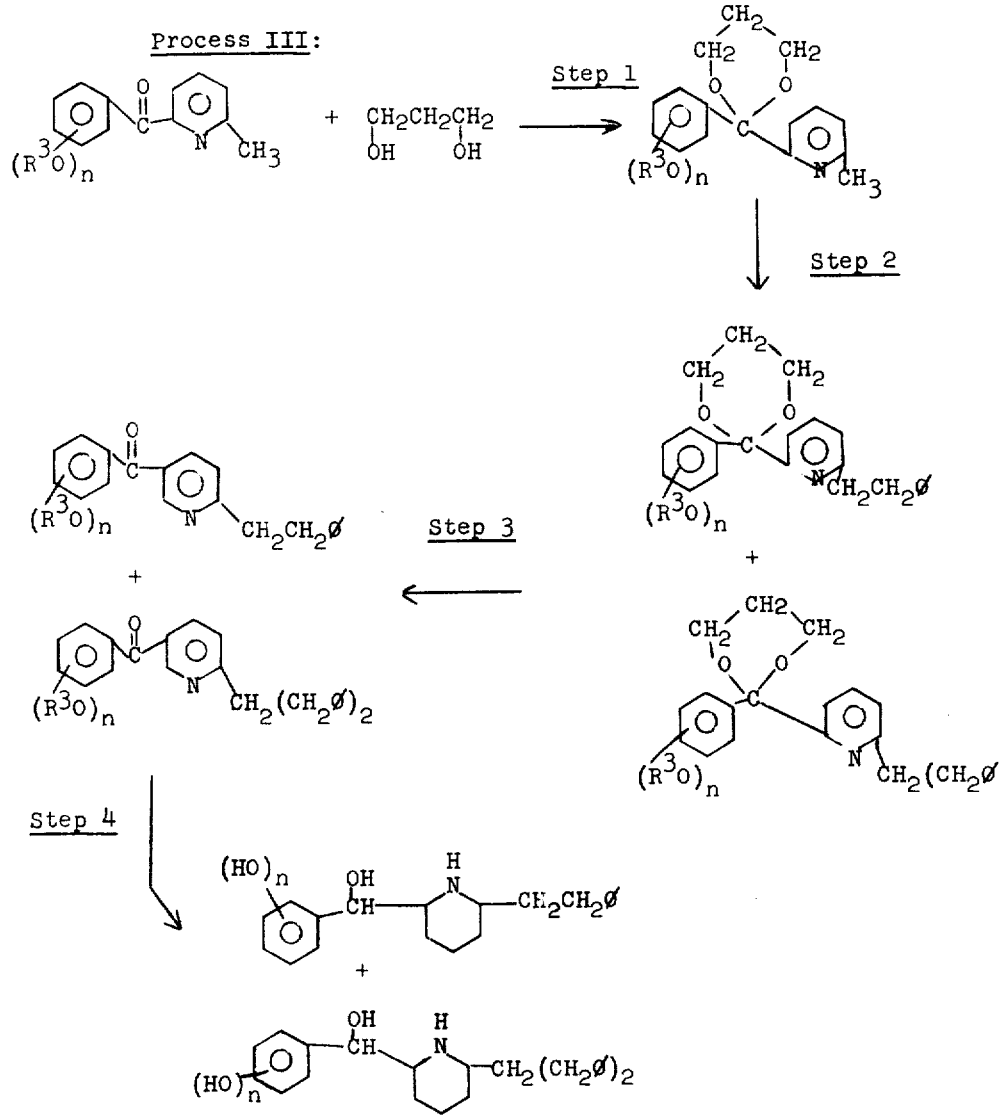

wherein $R^3$ is lower alkyl and $n$ is 2 or 3.

Step 1 comprises condensing a (poly-lower alkoxyphenyl) (6-2-pyridyl)ketone and 1,3-propanediol to form a 2-(poly-lower alkoxyphenyl)-2-(6-methyl-2-pyridyl)-1,3-dioxane intermediate. This intermediate is C-benzylated in Step 2 through treatment with phenyllithium followed by benzyl chloride to form a mixture of the 2-(poly-lower alkoxyphenyl)-2-(6-phenethyl-2-pyridyl)-1,3-dioxane and 2-(poly-lower alkoxyphenyl)-2-(6-dibenzylmethyl-2-pyridyl)-1,3-dioxane intermediate. Step 3 comprises demethylating and hydrolytically leaving the dioxane ring of this intermediate to form the (poly-hydroxyphenyl) (6-phenethyl-2-pyridyl)ketone and (poly-hydroxyphenyl) (6-2-pyridyl)ketone intermediates. These intermediates are hydrogenated in Step 4 to yield a separable mixture of the α-(poly-hydroxyphenyl)-α-(6-phenethyl-2-piperidinyl)methanol and α-(poly-hydroxyphenyl)-α-(6-dibenzylmethyl-2-piperidinyl)methanol final products.

In order to prepare compounds of the invention and II. The benzyloxy blocking group is removed by reduction, for example, with palladium on charcoal, rather than by ether cleavage methods. The latter methods may result in some cleavage of the phenoxy group as a side reaction and for this reason prove undesirable.

In general, however, it is possible to use phenyl, phenyl-lower alkyl and phenoxy-lower alkyl pyridine derivatives in Processes I and II described hereinabove for the preparation of compounds of this invention.

The starting materials for carrying out Process I of this invention are a phenyl, phenyl-lower alkyl or phenyl-lower alkoxy-substituted picolinic acid, and a poly(benzyloxy)-or poly-lower alkoxy-substituted benzaldehyde.

Poly-lower alkoxy benzaldehydes are conveniently prepared by the reduction of the corresponding acid chlorides by the Rosemund procedure [Ber. 51.585 (1918)] or by treatment with lithium tri-t-butyoxyaluminohydride, or by the oxidation of the corresponding benzyl alcohols, using, for example, manganese dioxide as an oxidizing agent.

Poly(benzyloxy)benzaldehydes are prepared by reacting polyhydroxybenzaldehydes with benzyl chloride in the presence of a base. This method is familiar to those skilled in the art.

Phenyl-lower-alkyl-substituted picolinic acids are prepared, for example, from lower alkyl-substituted picolinic acid esters or simple picolinic acid esters by reaction with butyl lithium followed by reaction with phenyl-lower alkyl halides such as benzyl bromide or dibenzyl bromide.

Phenoxy-lower-alkyl-substituted picolinic acids are prepared, for example, from lower alkyl-substituted picolinic acid esters by reaction with phenyl chloromethyl ether in the presence of strong base or by reaction of lower halo- and dihaloalkyl picolinic acids with phenoxide.

Examples of lower alkyl-substituted picolinic acids that may be used as a starting material include 6-benzylpicolinic acid, 6-phenylethylpicolinic acid, 6-phenoxyethylpicolinic acid and 6-diphenylmethylpicolinic acid. Among the poly-lower alkoxy-substituted benzaldehydes which may be used, but without limitation, are 2,3-dimethoxybenzaldehyde, 2,4-diethoxybenzaldehyde, 3,4-dimethoxybenzaldehyde, 2,4,6-trimethoxybenzaldehyde, 2,3,4-triethoxybenzaldehyde, 3,4,5-trimethoxybenzaldehyde, 3,5-dimethoxybenzaldehyde and the like.

In carrying out Process I, the 6-substituted picolinic acid and an appropriate poly-lower alkoxy-substituted benzaldehyde are condensed in Step 1 to form an $\alpha$-(poly-lower alkoxyphenyl)-$\alpha$-(6-substituted-2-pyridinyl)methanol wherein the substitution on the phenyl and pyridine rings corresponds to that in the starting materials. The condensation reaction is carried out in the presence of an inert solvent medium; such as p-cymene, nitrobenzene, or anisole; and at a temperature above 140°C. The preferred temperature is the reflux temperature of the solvent used. The product of the reaction is recovered by conventional procedures of isolation and crystallization.

In Step 2, the unpurified $\alpha$-(poly-lower alkoxyphenyl)-$\alpha$-(6-substituted-2-pyridinyl)methanol intermediate thus formed is treated with a strong oxidizing agent such as, for example, potassium permanganate, dimethyl sulfoxide-acetic anhydride or dry air, and the like to form the corresponding (poly-lower alkoxy-phenyl) (6-substituted 2-pyridyl)ketone. When the oxidizing agent is potassium permanganate, the oxidation reaction may be carried out in an aqueous solvent medium and at a temperature not exceeding about 80°C. The product is recovered by conventional methods of isolation and purification. This product is then dealkylated in Step 3 to form a (polyhydroxyphenyl) (6-substituted-2-pyridyl)ketone. The dealkylation is preferably accomplished by heating a solution of the ketone in constant boiling hydrobromic acid under reflux.

In the final step of the reaction sequence, the (polyhydroxyphenyl) (6-substituted-2-pyridyl)ketone is hydrogenated in the presence of a catalyst, e.g., Adams platinum catalyst or platinum on a charcoal support. The hydrogenation is carried out in the presence of an inert organic solvent, e.g., methanol, ethanol or acetic acid, and the like, at atmospheric pressure and at a temperature of 20°–60°C. The $\alpha$-(polyhydroxyphenyl)-$\alpha$-(6-substituted-2-piperidinyl)methanol final product is recovered by conventional procedures for isolation and purification.

The starting materials for carrying out Process II are 6-substituted 2-pyridyllithium (which may be prepared by treatment of 6-substituted or 2-bromopyridine in ether solution with freshly cut metallic lithium) and 4-benzyloxy-3-methoxybenzaldehyde or other alkoxy-substituted benzaldehydes. The latter materials may be prepared, for example, by refluxing vanillin with benzyl chloride.

In carrying out Step 1 of Process II, a solution of the 4-benzyloxy-3-methoxybenzaldehyde in an anhydrous inert organic solvent such as anhydrous ether is slowly added to a solution of 6-substituted 2-pyridiyllithium in an anhydrous inert organic solvent such as anhydrous diethyl ether. The temperature of the two solutions should be between 0° to −20°C. The resulting mixture is allowed to warm to room temperature. Upon treatment of the reaction mixture with a mineral acid, e.g., hydrochloric acid, the $\alpha$-(lower-alkoxy-p-benzyloxyphenyl)-$\alpha$-(6-substituted-2-pyridinyl)methanol intermediate forms and is recovered by conventional techniques of separation and crystallization.

The benzyl protecting group of the methanol intermediate is removed in Step 2 by hydrogenation in an inert organic solvent, e.g., methanol, in the presence of a prereduced palladium or palladium on charcoal catalyst. The hydrogenation is carried out at room temperature and atmospheric pressure. The $\alpha$-(lower-alkoxy-p-hydroxyphenyl)-$\alpha$-(6-substituted-2-pyridinyl)methanol intermediate thus formed is recovered by conventional procedures of isolation and purification. This material is then converted in Step 3 to the corresponding $\alpha$-(lower-alkoxy-p-hydroxyphenyl)-$\alpha$-(6-substituted-2-piperidinyl)-methanol final product by hydrogenation in the presence of catalyst such as Adams platinum catalyst or platinum on a charcoal support. The final products are recovered by conventional methods of isolation and purification.

The starting material for carrying out Process III is a (poly-lower alkoxyphenyl) (6-methyl-2-pyridyl) ketone. This material can be prepared by following Steps 1 and 2 of Process I using 6-methyl picolinic acid as a starting material.

In carrying out Step 1 of Process III, the substituted-2-pyridyl ketone starting material is condensed with 1,3-propanediol. The condensation is carried out in an inert organic solvent, e.g., toluene, at the reflux temperature of the solvent in the presence of p-toluenesulfonic acid catalyst. The product formed is 2-(poly-lower-alkoxyphenyl)-2-(6-methyl-2-pyridyl)-1,3-dioxane.

In Step 2, this intermediate is treated first with phenyllithium reagent and then with benzyl chloride in an inert anhydrous organic solvent, e.g., tetrahydrofuran. The latter reaction is carried out at the reflux temperature of the solvent and under nitrogen atmosphere. A mixture of 2-(poly-lower alkoxy-phenyl)-2-(6-phenethyl-2-pyridyl)-1,3-dioxane and 2-(1-poly-lower alkoxyphenyl)-2-(6-dibenzylmethyl-2-pyridyl)-1,3-dioxane is produced. These intermediates are separated and recovered by conventional methods of isolation and purification.

The phenethyl- and dibenzylmethyl-substituted intermediates are treated in Step 3 with hydrobromic acid at reflux temperatures to cause demethylation and simultaneous opening of the dioxane ring to form the ketone. Products of the reaction are (polyhydroxyphenyl) (6-phenethyl-2-pyridyl)ketone and (polyhydroxyphenyl)

(6-dibenzylmethyl-2-pyridyl)ketone. These intermediates are recovered by conventional methods of isolation and purification. In the final step of this process, these intermediates are converted to the α-(polyhydroxyphenyl)-α-(6-phenethyl-2-piperidinyl)methanol and α-(polyhydroxyphenyl)-α-(6-dibenzylmethyl-2-piperidinyl)methanol final products by hydrogenation in the presence of catalyst such as Adams platinum catalyst or platinum on a charcoal support. As is obvious to one skilled in the art, it is possible to vary the processes described herein and to combine steps from more than one process to prepare the compounds of the invention.

The compounds of this invention have significant pharmacological activity as bronchodilator agents. The preferred compounds of the present invention have been found to possess bronchodilator activity that is equivalent to, or better than, that possessed by the known bronchodilator agent aminophylline. The compounds were evaluated in vivo in the guinea pig and the dog, and in vitro in an isolated tissue bath employing guinea pig tracheal tissue. Doses and concentrations employed were comparable to those of the aminophylline standards. All of the methods used for the evaluation of compounds of the invention are recognized and accepted in the art of pharmacology for the evaluation of bronchodilator activity.

The compounds of this invention may be administered orally, parenterally or by inhalation in conventional dosage forms.

The compounds of this invention, either as free bases or in the form of a pharmaceutically accepted acid-addition or quaternary ammonium salt, can be combined with conventional pharmaceutical diluents and carriers to form such dosage forms as tablets, capsules, suspensions, solutions, suppositories and the like.

The individual unit dosage and frequency of administration is determined, not only by the nature and severity of the condition for which the subject seeks relief, but also upon age, weight, and species of subject, the underlying physical condition of the subject and the route of administration of the compound. It is, accordingly, within the judgment and skill of the practitioner administering the drug to determine the exact amount to be administered so as to be non-toxic, yet pharmaceutically effective in promoting bronchodilation. When administered orally, between 0.5 and 10 milligrams of active ingredient per kilogram of body weight, 3 to 4 times daily, will usually be sufficient to provide the desired effect.

Useful pharmaceutical carriers or diluents for the compounds of the invention may be either solid or liquid. Conventionally used solid carriers include lactose, terra alba, sucrose, talc, gelatin, agar, pectin, acacia, magnesium stearate, steric acid, and the like. Liquid carriers may include syrups, peanut oil, olive oil, water and the like. The carrier or diluent may include any timed-release material well known to the art, such as glyceryl monostearate or glyceryl distearate, alone or with a wax.

A wide variety of pharmaceutical forms can be employed. If a solid carrier is used, the preparation can be tableted, placed in a hard gelatin capsule in powder or pellet form, or made into the form of a troche or lozenge. The amount of solid carrier will vary widely but, preferably, will be between 25 mg. and 1 g. If a liquid carrier is used, the preparation will be in the form of a syrup, emulsion, solt gelatin capsule, sterile injectable liquid such as an ampule, or an aqueous or non-aqueous liquid suspension. Of particular applicability for inhalation administration is an aerosol dispensing system wherein the active medicament is incorporated with Freon or other inert propellant in an aerosol container. Such as aerosol system will deliver a metered dose of about 250 mcg., administered once or twice at a time as needed. Also useful for this purpose is a liquid formulation in a plastic squeeze bottle.

The following examples illustrate the preparation of the compounds of the present invention.

EXAMPLE I (Preparation of starting materials for Process III)

Step 1.
α-(3,4-DIMETHOXYPHENYL)-α-(6-METHYL-2-PYRIDINYL)METHANOL

Ten g. of 6-methylpicolinic acid were added to a boiling solution of 50 g. of 3,4-dimethoxybenzaldehyde in 50 ml of p-cymene over a period of 3 hours. After the addition was completed, heating was continued for 3 hours. The reaction was then allowed to cool. The cooled reaction mixture was extracted twice with a total of 100 ml of 2N hydrochloric acid. The combined acid extract was washed with 100 ml of diethyl ether, made basic with ammonia solution and then extracted four times with a total of 200 ml of ether. The combined ether extracts were concentrated to dryness to produce an oil which yielded α-(3,4-dimethoxyphenyl)-α-(6-methyl-2-pyridinyl)methanol from a solution of acetonepetroleum ether (b.p. 60°–80°C.)

Step 2. (3,4-DIMETHOXYPHENYL) (6-METHYL-2-PYRIDYL) KETONE

Ten g. of α-(3,4-dimethoxyphenyl)-α-(6-methyl-2-pyridinyl) methanol were suspended with stirring in 200 ml of water. This mixture was warmed to 10°C. Potassium permanganate was then added to the mixture in small portions until the pink coloration was discharged; a total of 4.7 g. was added. Excess permanganate was destroyed by the addition of ethanol and the manganese dioxide thus formed was removed by filtration. The filter cake was extracted three times with a total of 300 ml of boiling industrial methylated spirit. The filtrate was then concentrated under reduced pressure until crystallization commenced. The white needles were collected by filtration, washed with water, and dried in vacuo to give (3,4-dimethoxyphenyl) (6-methyl-2-pyridyl) ketone m.p., 84°–86°C.

Using the method of Example 1, in step 1, 3,5-dimethoxybenzaldehyde was reacted with 6-methylpicolinic acid to provide α-(3,5-dimethoxyphenyl)-α-(6-methyl-2-pyridinyl)methanol, m.p. 85°–88°C. Analysis: Calculated for $C_{15}H_{17}NO_3$: %C, 69.5; %H, 6.6; %N, 5.4; Found: %C, 69.6; %H, 6.7; %N, 5.4.

In step 2 the product of step 1 was oxidized to 3,5-dimethoxyphenyl 6-methyl-2-pyridyl ketone.

EXAMPLE 2 (Process III)

Step 1.
2-(3,4-DIMETHOXYPHENYL)-2-(6-METHYL-2-PYRIDYL)-1,3-DIOXANE

About 77.1 g. of (3,4-dimethoxyphenyl) (6-methyl-2-pyridyl) ketone, 74.1 g. of p-toluenesulfonic acid and 22.8 ml of 1,3-propanediol in 600 ml of toluene were heated under reflux with stirring for 17 hours. The water evolved during the reaction was neutralized with 500 ml of saturated sodium bicarbonate. Two phases formed and the phases were separated. The organic layer was washed with saturated sodium bicarbonate solution and dried over magnesium sulfate. Removal of the desiccant and solvent gave a solid residue which, on recrystallization from a mixture of acetone and petroleum ether (b.p. 60°–80°C.), yielded 2-(3,4-dimethoxyphenyl)-2-(6-methyl-2-pyridyl)-1,3-dioxane, m.p. 124°–126°C.

Step 2.
2-(3,4-DIMETHOXYPHENYL)-2-(6-PHENETHYL-2-PYRIDYL)-1,3-DIOXANE and
2-(3,4-DIMETHOXYPHENYL)-2-(6-DIBENZYL-METHYL-2-PYRIDYL)-1,3-DIOXANE About 8.7 ml of bromobenzene in 20 ml. of dry ether were added to a stirred suspension of 1 g. lithium shavings in 50 ml. of dry ether under a nitrogen atmosphere over a period of 30 minutes. This rate of addition was sufficient to maintain the reaction at a gentle reflux. After the addition, the mixture was stirred for 1.5 hours, followed by the addition of 18.9 g. of 2-(3,4-dimethoxyphenyl)-2-(6-methyl-2-pyridyl)-1,3-dioxane which was dissolved in the minimum quantity of dry tetrahydrofuran. Eight g. of benzyl chloride in 10 ml. of dry tetrahydrofuran were then added dropwise at such a rate that gentle boiling occurred. When this addition was completed, the reaction mixture was stirred for 0.5 hour. Lithium complexes were decomposed by the addition of saturated ammonium chloride solution and phase separation occurred. The organic layer was diluted with 200 ml. of diethyl ether and then extracted twice with a total of 200 ml. of 2N hydrochloric acid. The acid extract was washed with 100 ml. of diethyl ether, basified with ammonia solution and the liberated basic products were extracted twice into a total of 120 ml. of chloroform. Concentration of the dried extracts produced a syrup which was applied to a 30 × 4 cm column of silica gel and eluted with a 4:1 mixture of chloroform/ethyl acetate. Twenty-four successive fractions of 25 ml. each were collected and examined by thin layer chromatography. Three main components were detected in the reaction mixture. The slowest moving compound had an identical mobility to that of the starting material. Fractions 1 to 13 were discarded since no product was detected. Fractions after 24 were discarded because they contained increasing amounts of starting material. Fractions 14 to 16 and 17 and 18 gave crystalline material upon trituration with ethanol and had identical infrared spectra. (No carbonyl functions were present). Recrystallation of this material from ethanol yielded 2-(3,4-dimethoxyphenyl)-2-(6-dibenzylmethyl-2-pyridyl)-1,3-dioxane, m.p. 124°C. Analysis: Calculated for $C_{32}H_{33}NO_4$: C, 77.55; H, 6.7; N, 218. Found: C, 77.65; H, 6.8; N, 3.0.

Fractions 19 to 21 and 22 to 24 slowly crystallized and recrystallization from industrial methylated spirit gave 2-(3,4-dimethoxyphenyl)-2-(6-phenylethyl-2-pyridyl)-1,3-dioxane, m.p. 86°–87°C. Analysis: Calculated for $C_{25}H_{27}NO_4$: C, 74.05; H, 6.7; N, 3.45. Found: C, 74.1; H, 6.6; N, 3.6.

Step 3a. (3,4-DIHYDROXYPHENYL)
(6-PHENETHYL-2-PYRIDYL) KETONE HYDROBROMIDE

A solution of 3.5 g. of 2-(3,4-dimethoxyphenyl)-2-(6-phenylethyl-2-pyridyl)-1,3-dioxane in 20 ml. of 48% hydrobromic acid was heated under reflux for 20 hours. The solvent was removed under reduced pressure and industrial methylated spirit was evaporated several times from the residue which crystallized upon trituration with ethyl acetate. Recrystallization from methanolethyl acetate yielded (3,4-dihydroxyphenyl) (6-phenylethyl-2-pyridyl) ketone hydrobromide, m.p. 181°C. Analysis: Calculated for $C_{20}H_{18}NO_3Br$: C, 60.0; H, 4.5; N, 3.5; Br, 20.0. Found: C, 60.2; H, 4.7; N, 3.6; Br, 20.35.

b. (3,4-DIHYDROXYPHENYL)
(6-dibenzylmethyl-2-PYRIDYL) KETONE

A solution of 2.0 g. of 2-(3,4-dimethoxyphenyl)-2-(6-dibenzylmethyl)-2-pyridyl)-1,3-dioxane in 20 ml. of constant boiling hydrobromic acid was heated under reflux for 16 hours. The free base was liberated with ammonia solution and extracted twice into a total of 100 ml. of ether. Removal of the solvent from the dried extracts gave a syrupy residue which on crystallization from ether-petroleum ether (b.p. 60°–80°C.) yielded (3,4-dihydroxyphenyl) (6-dibenzylmethyl-2-pyridyl) ketone, m.p. 141°–143°C.

Step 4a.
erythro-α-(3,4-DIHYDROXYPHENYL)-α-(6-PHENETHYL-2-PIPERIDINYL) METHANOL HYDROBROMIDE Two g. of (3,4-dihydroxyphenyl) (6-phenylethyl-2-pyridyl) ketone hydrobromide in 100 ml. of methanol were hydrogenated in the presence of 0.2 g. of Adams platinum catalyst at atmospheric pressure and room temperature. After 4 moles of hydrogen had been consumed, the catalsyt and solvent were removed to give a syrup from which a 100 mg sample was removed for nuclear magnetic resonance spectroscopic analysis. The remainder was crystallized from a mixture of methanol-ethyl acetate to give erythro-α-(3,4-dihydroxyphenyl)-α-(6-phenethyl-2-piperidinyl) methanol hydrobromide, m.p. 204°C.

Analysis: Calculated for $C_{20}H_{26}NO_3Br$: C, 58.8; H, 6.4; N, 3.4; Br, 19.6. Found: C, 58.6; H, 6.6; N, 3.5; Br, 19.9.

b.
α-(3,4-DIHYDROXYPHENYL)-α-(6-DIBENZYL-METHYL-2-PIPERIDINYL) METHANOL

A solution of 1.2 g. of (3,4-dihydroxyphenyl) (6-dibenzylmethyl-2-pyridyl) ketone in 100 ml. of methanol and 0.585 ml. of 5M hydrochloric acid was hydrogenated in the presence of 0.3 g. of Adams platinum catalyst at atmospheric pressure and room temperature. After the theoretical quantity of hydrogen had been consumed, the catalyst and solvent were removed to give a syrup. The evaporation of ethyl acetate from the residue produced a dry froth which was powdered under ether, collected by filtration, and dried in vacuo. Yield: 1.22 g.

EXAMPLE 3

Preparation of
α-(3,5-dihydroxyphenyl)-α-(6-benzyl-2-piperidinyl)-methanol

1. α-phenyl-α-(6-ethoxy-2-pyridyl)methanol

A solution of 51.52 g. of 2-bromo-6-ethoxypyridine in 40 ml. of diethyl ether was added to a solution of butyl lithium (prepared from 2.22 g. of lithium and 21.52 g. of 1-bromobutane in 140 ml. of ether at −20° to −10°C.). To this mixture were added 16.6 g. of benzaldehyde in 40 ml. of dry ether at the same temperature. After the addition, the mixture was allowed to warm up to room temperature, and was extracted twice with a total of 200 ml. of 2N hydrochloric acid. Basification of the acid layers gave the product which was extracted three times into a total of 195 ml. of chloroform. Removal of the solvent and distillation of the residue yielded the pure product, b.p. 140°c./0.5 m.m. Hg.

2. 2-Benzyl-6-ethoxypyridine

A solution of 189 g. of α-phenyl-α-(6-ethoxy-2-pyridyl) methanol in 500 ml. of methanol was hydrogenated at room temperature and atmospheric pressure over 45 g. of 10% palladium on charcoal. After 1 mole of hydrogen had been consumed the catalyst and solvent were removed and the residue was distilled to give the product, b.p. 118°–120°/0.5 m.m. It was reacted with hydrogen chloride in diethyl ether to give its hydrochloride salt, m.p. 103°C.

Analysis: Calculated for: $C_{14}H_{15}NO \cdot HCl$: %C, 67.3; %H, 6.5; %N, 5.6; %Cl, 14.2. Found: %C, 67.35; %H, 6.5; %N, 5.7; %Cl, 14.0.

3. 2-Benzyl-6-bromopyridine

One hundred fifteen g. of 2-benzyl-6-ethoxypyridine and 200 g. of phosphorous oxybromide were heated together with stirring at 135°C. for 1 hour. The mixture gave off a gas during the first 15 minutes of the reaction but remained calm for the rest of the heating period. On cooling, the mixture became an intractable tar and the reaction flask was broken to obtain the crude product. It was partitioned between 2 liters of water, 270 ml. of 10N sodium hydroxide solution and 1 liter of chloroform. The organic extract was washed with 1 liter of water and dried over magnesium sulfate. Removal of the desiccant and solvent yielded a dark oil which was extracted with 750 ml. of petroleum ether (b.p. 60°–80°C.), and treated with decolorizing charcoal. Removal of the solids and solvent yielded the product as an amber oil. This material was used without further purification for the next step.

4. α-(3,5-Dimethoxyphenyl)-α-(6-benzyl-2-pyridyl)methanol hydrochloride

About 5.7 g. of 2-benzyl-6-bromopyridine in 15 ml. of hexane were added to a solution of n-butyl lithium (prepared from 0.48 g. of lithium and 4.75 g. of 1 bromobutane in 40 ml. of hexane at −20°C. Then 5.7 g. of 3,5-dimethoxybenzaldehyde in 30 ml. of toluene were added at the same temperature and the mixture was allowed to warm at room temperature.

Fifty milliliters of water were added and the phases were separated. The organic layer was washed with 50 ml. of water and dried over magnesium sulfate. The dried solution was treated with hydrogen chloride and the precipitated tacky solid was collected, washed with diethyl ether and recrystallized from an ether-isopropanol mixture to give the desired product.

Analysis: Calculated for $C_{21}H_{21}NO_3Cl$: %C, 67.8; %H, 6.0; %N, 3.8; %Cl, 9.5. Found: %C, 68.0; %H, 6.0; %N, 3.0.

Nuclear magnetic resonance spectroscopy confirmed the assigned structure.

5. 3,5-dimethoxyphenyl 6-benzyl-2-pyridinyl ketone

About 15.5 g. of α-(3,5-dimethoxyphenyl)-α-(6-benzyl-2-pyridinyl)methanol from Step (d) was dissolved in 100 ml. of water and 200 ml. of acetone. The solution was treated with 10 g. of potassium permanganate added in two portions over 15 minutes. The extent of the reaction was monitored by thin layer chromatography (eluent 9:1 chloroform - ethyl acetate) and when all the starting material had reacted, the excess permanganate was destroyed with ethanol. Removal of the solids by filtration followed by evaporation of the solvent gave a syrup which was extracted with chloroform. The dried organic layer yielded a syrup upon concentration and this was dissolved in diethyl ether and treated with hydrogen chloride. The precipitated salt was collected, washed with ether and dried in vacuo to yield 3,5-dimethoxyphenyl 6-benzyl-2-pyridinyl ketone hydrochloride, m.p. 51°–110°. The free pyridyl ketone prepared by treatment of this salt with base had m.p. 53°–55°.

Analysis: Calculated for $C_{21}H_{19}NO_3$: %C, 75.65; %H, 5.7; %N, 4.2 Found: %C, 76.0; %H, 5.6; %N, 4.3.

6. 3,5-dihydroxyphenyl 6-benzyl-2-pyridyl ketone hydrochloride

About 15.5 g. of 3,5-dimethoxyphenyl 6-benzyl-2-pyridyl ketone hydrochloride in 55 ml. of constant boiling hydrobromic acid were heated under reflux for 12 hours. Removal of the solvent gave a tacky residue which was basified with ammonia solution and was extracted three times with a total of 90 ml. of boiling ethyl acetate. The extracts were washed twice with a total of 50 ml. of water, dried over magnesium sulfate and treated with charcoal. Removal of the solids and treatment of the filtrate with hydrogen chloride yielded 3.52 g. of a khaki-colored salt. Nuclear magnetic spectroscopy revealed that the methoxy groups had been removed and the product was used without further purification for the next step.

7. α-(3,5-dihydroxyphenyl)-α-(6-benzyl-2-piperidinyl)-methanol hydrochloride

A solution of 7.85 g. of 3,5-dihydroxyphenyl 6-benzyl-2-pyridyl ketone hydrochloride in 100 ml. of methanol was hydrogenated over 2.0 g. of palladium on charcoal. After 4 moles of hydrogen had been consumed, the catalyst was removed by filtration and the solvent was removed by evaporation. The residue was suspended in 30 ml. of water and basified with ammonia solution. The solid product (m.p. 120°C.) was collected, washed well with water and dried in vacuo over calcium chloride. After two recrystallizations from ethyl acetate, the pure base erythro-α-(3,5-dihydroxyphenyl)-α-(6-benzyl-2-piperidinyl)methanol was obtained, m.p. 219°.

Treatment of this base with hydrogen chloride in diethyl ether/isopropanol gave the hydrochloride salt, m.p. 255°/dec. Analysis: $C_{19}H_{22}NO_3 \cdot HCl$: %C, 65.2; %H, 6.9; %N, 4.0; %Cl, 10.1. Found: %C, 65.4; %H, 6.9; %N, 3.95; %Cl, 10.4.

EXAMPLE 4

α-(3,5-dihydroxyphenyl)-α-(6-phenethyl-2-piperidinyl)-ketone methanol hydrochloride 3,5-Dihydroxyphenyl 6-methyl-2-pyridyl ketone is prepared according to example 1 from 3,5-dimethoxybenzaldehyde and 6-methyl picolinic acid. This intermediate is then reacted according to example 2 and purified to yield pure erythro-α-(3,5-dihydroxyphenyl)-α-(6-phenethyl-2-piperidinyl)methanol hydrochloride, m.p. 285°C.

Analysis: Calculated for: $C_{20}H_{25}NO_3 \cdot HCl$; %C, 66.0; %H, 7.2; %N, 3,85; %Cl, 9.7. Found: %C, 66.2; %H, 712; %N, 3.9; %Cl, 9.9.

EXAMPLE 5

α-(3,5-Dihydroxyphenyl)-α-(6-phenethyl-2-piperidinyl) methanol hydrochloride of example 4 was tested for bronchodilator activity according to conventional testing methods. Results of the tests were as follows:

a. ISOLATED ORGANS

The test compound showed significant spasmolytic activity when tested on the isolated guinea pig tracheal chain at a dose of 5 mcg per ml. of tissue bath solution. This test method is described by K. W. Dengan et al. in J. of Pharmacol Exp. Ther. 164: 290–301, 1968.

b. ANESTHETIZED ANIMALS

The test compound inhibited histamine-induced bronchospasm in the anesthetized artifically-respired dog. The test compound had activity when administered intravenously or intraduodenally at a dose of 100 mcg/kg of body weight. This test method is described by Konzett and Rossler in Arch. Exp. Path. Pharmak. 195: 71, 1940.

c. CONSCIOUS ANIMALS

The test compound reduced the severity of the anaphylactic reaction in sensitized guinea pigs challenged by inhalation of histamine antigen. This test is described in U.S. Pat. No. 3,248,292.

The test compound had oral activity with long duration of action at doses of 9 to 100 mg/kg of body weight.

EXAMPLE 6

The following compounds of the invention are prepared using the method of Process I from the starting materials shown preceding them.

Table 1

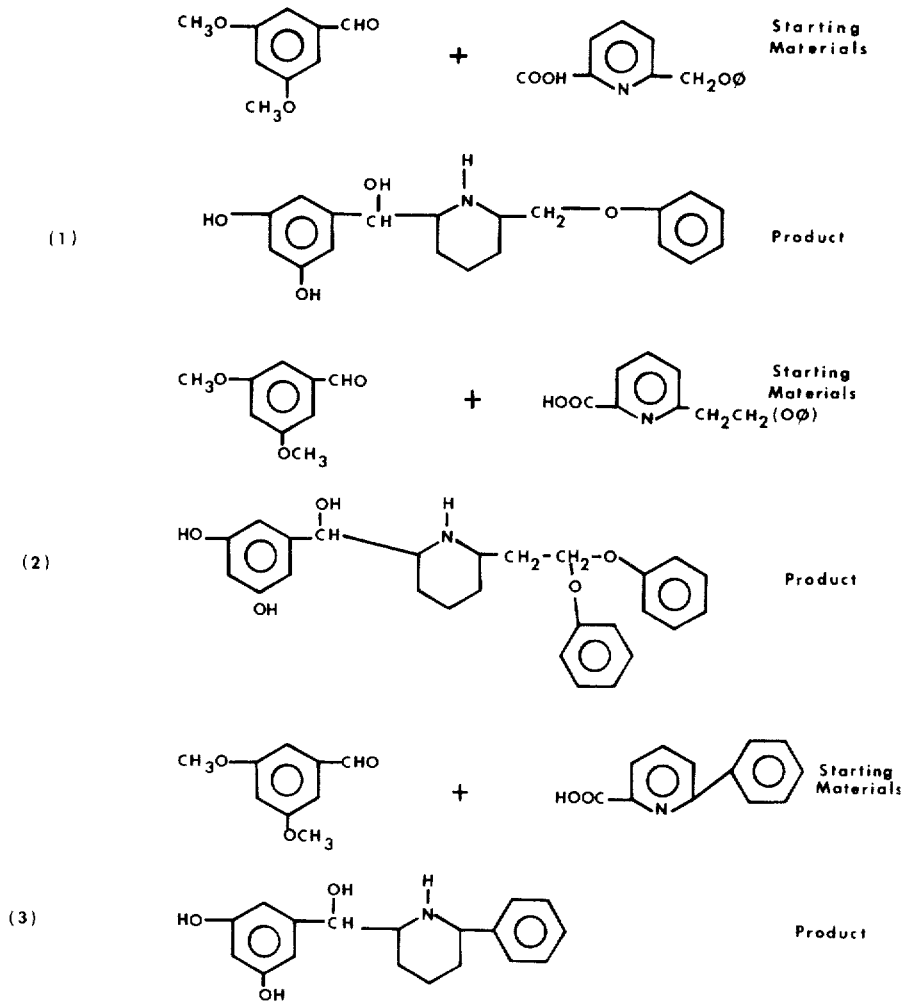

What is claimed is:
1. A compound of the formula

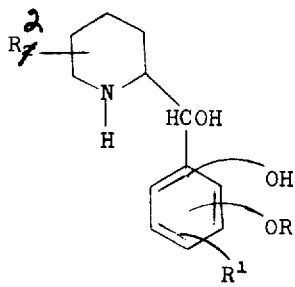

wherein R is hydrogen or lower alkyl, R¹ is hydrogen, hydroxy or lower alkoxy and R² is phenyl, phenyl-lower alkyl, diphenyl-lower alkyl, phenoxy-lower alkyl or diphenoxy-lower alkyl and the nontoxic pharmaceutically acceptable acid addition and quaternary ammonium salts thereof.

2. A compound of the formula

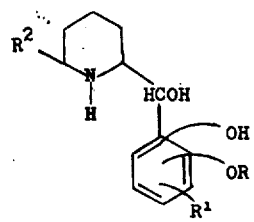

wherein R is hydrogen or lower alkyl, R¹ is hydrogen, hydroxy or lower alkoxy, and R² is phenyl, phenyl-lower alkyl, diphenyl-lower alkyl, phenoxy-lower alkyl or diphenoxy-lower alkyl, and the pharmaceutically acceptable acid-addition and quarternary ammonium salts thereof.

3. A compound according to claim 2 wherein R² is phenyl-lower alkyl or diphenyl-lower alkyl.

4. The compound α-(3,4-dihydroxyphenyl-α-(6-phenethyl-2-piperidinyl) methanol, and pharmaceutically acceptable salts thereof, according to claim 3.

5. The compound α-(3,4-dihydroxyphenyl)-α-(6-dibenzylmethyl-2-piperidinyl)methanol and pharmaceutically acceptable salts thereof according to claim 3.

6. The compound α-(3,5-dihydroxyphenyl)-α-(6-phenethyl-2-piperidinyl) methanol and pharmaceutically acceptable salts thereof according to claim 3.

7. The compound α-(3,5-dihydroxyphenyl)-α-(6-benzyl-2-piperidinyl) methanol and pharmaceutically acceptable salts thereof according to claim 3.

* * * * *

UNITED STATES PATENT AND TRADEMARK OFFICE
CERTIFICATE OF CORRECTION

PATENT NO. : 3,941,796
DATED : March 2, 1976
INVENTOR(S) : GEORGE H. SANKEY AND KEITH D. E. WHITING It is certified that error appears in the above-identified patent and that said Letters Patent are hereby corrected as shown below:

Col. 2, line 6, change "3 or" to -- 3 and --.

Col. 6, second formula below step 2, change "  "

to --  --.

Col. 5, line 52, change "(6-2-pyridyl)" to -- (6-methyl-2-pyridyl --.

Col. 5, line 63, change "(6-2-pyridyl)" to -- (6-dibenzylmethyl-2-pyridyl) --.

Col. 8, line 5, change "6-substituted or 2-bromopyridine" to -- 6-substituted 2-chloro- or 2-bromopyridine --.

Col. 13, line 66, change "3.0" to -- 3.9 --.

Signed and Sealed this

Eighteenth Day of January 1977

[SEAL]

Attest:

RUTH C. MASON
Attesting Officer

C. MARSHALL DANN
Commissioner of Patents and Trademarks